United States Patent
Fay

(10) Patent No.: US 11,991,817 B2
(45) Date of Patent: May 21, 2024

(54) HIGH INTENSITY NARROW SPECTRUM AND FAR UVC PROTECTION DEVICE

(71) Applicant: LUX Lighting Systems LLC, Keizer, OR (US)

(72) Inventor: Jonathan Eric Fay, Keizer, OR (US)

(73) Assignee: LUX LIGHTING SYSTEMS LLC, Keizer, OR (US)

( * ) Notice: Subject to any disclaimer, the term of this patent is extended or adjusted under 35 U.S.C. 154(b) by 446 days.

(21) Appl. No.: 17/207,109

(22) Filed: Mar. 19, 2021

(65) Prior Publication Data

US 2021/0298164 A1 Sep. 23, 2021

Related U.S. Application Data

(60) Provisional application No. 62/991,757, filed on Mar. 19, 2020.

(51) Int. Cl.
*H05K 1/00* (2006.01)
*A61L 2/10* (2006.01)
(Continued)

(52) U.S. Cl.
CPC .............. *H05K 1/0206* (2013.01); *A61L 2/10* (2013.01); *H05K 7/20136* (2013.01);
(Continued)

(58) Field of Classification Search
CPC ............. H05K 1/0206; H05K 7/20136; H05K 7/2039; H05K 2201/09018; H05K 2201/10106; H05K 2201/10121; A61L 2/10; A61L 2202/11; A61L 2202/16; A61N 5/0624; A61N 2005/0633;
(Continued)

(56) References Cited

U.S. PATENT DOCUMENTS

| | | | | |
|---|---|---|---|---|
| 2015/0037201 A1* | 2/2015 | Armour | ............. | A61B 90/06 600/203 |
| 2015/0306263 A1* | 10/2015 | Yanke | ............. | A61L 2/00 250/455.11 |
| 2023/0103086 A1* | 3/2023 | Bae | ............. | A61L 2/24 250/455.11 |

OTHER PUBLICATIONS

John Wallace; "HINS light kills surface bacteria in hospitals"; https://www.laserfocusworld.com/test-measurement/research/article/16567772/hins-light-kills-surface-bacteria-in-hospitals; LaserFocusWorld; Nov. 2010; accessed Apr. 2, 2021; 12 pages.

* cited by examiner

*Primary Examiner* — Michael Maskell
(74) *Attorney, Agent, or Firm* — BakerHostetler

(57) ABSTRACT

The disclosure describes an antimicrobial protection device using antibacterial and virucidal electromagnetic energy to provide protection. Electromagnetic energy may be supplied by light source(s) such as LED(s). Lighting apparatus may be configured to project electromagnetic energy in an energy barrier over an individual or portion thereof, such as the individual's airways and eyes. Light source(s) may be constructed or configured to emit electromagnetic energy in wavelengths at about 405 nm and/or between about 200 nm to about 220 nm. Lighting apparatus may be configured in a ring and may be mounted above the user's head such that the lighting apparatus projects a bactericidal and/or virucidal curtain of light around the user's head, killing or inactivating microbes before reaching the user's eyes, nose, or mouth. Apparatus of the present disclosure may be useful for medically fragile children (including those in wheelchairs), medically fragile people, and medical personnel in high-risk infectious areas.

22 Claims, 7 Drawing Sheets

(51) Int. Cl.
  *H05K 1/02* (2006.01)
  *H05K 7/20* (2006.01)
(52) U.S. Cl.
  CPC ........ *H05K 7/2039* (2013.01); *A61L 2202/11* (2013.01); *A61L 2202/16* (2013.01); *H05K 2201/09018* (2013.01); *H05K 2201/10106* (2013.01); *H05K 2201/10121* (2013.01)
(58) Field of Classification Search
  CPC .... A61N 2005/0651; A61N 2005/0661; A61N 2005/0662
  USPC ............................ 250/454.11, 455.11, 504 R
  See application file for complete search history.

HIGH INTENSITY NARROW SPECTRUM AND FAR UVC PROTECTION DEVICE

CROSS REFERENCE TO RELATED APPLICATION

This application claims priority to U.S. Provisional Application Ser. No. 62/991,757 filed Mar. 19, 2020, the entire disclosure of which is incorporated by reference

BACKGROUND OF THE INVENTION

High Intensity Narrow Spectrum (or "HINS") light is a narrow band of visible light that can kill microorganisms, including many infectious bacteria, without being harmful to humans. Light with a wavelength of between about 400-420 nm, and more particularly about 405 nm, may excite molecules within the microorganisms, and/or cause reactive molecules to be generated within the microorganisms, which may lead to death or inactivation of the microorganisms. A treatment using HINS light may clean and disinfect the air and any surfaces that the light contacts. Hospitals around the world are adopting HINS light decontamination treatment, particularly in burn units and units having patient populations highly susceptible to contracting infection, to control the spread of antibiotic-resistant strains of microorganisms such as MRSA and *Clostridioides difficile* ("C-Diff."). Traditional methods for decontamination including chemical liquid and gas disinfectants and UV lights can be harmful to humans. Additionally, conventional cleaning, disinfecting, mask wearing, and hand washing may have limited effectiveness and may be prone to human error.

Far UVC light, having wavelengths of between about 207 nm to about 222 nm, may also kill or inactivate microorganisms. Far UVC light may penetrate small microorganisms like bacteria and viruses, causing molecular changes and/or development of reactive molecules that may kill or inactivate the microorganism. Far UVC light may interact with genetic material (DNA or RNA), causing mutations fatal to the microorganism or that inhibit the microorganism's reproduction. As an example, far UVC light may dimerize pyrimidine bases and may lead to structural degradation of proteins, including the outer protein casing of many viruses. Far UVC light may also be safer for humans than conventional germicidal UV light; while far UVC light may be capable of penetrating microorganisms, it has very limited penetration depth on larger organisms like humans. Far UVC has shown potential to kill or inactivate airborne viruses, including the influenza strain H1N1 and the SARS coronavirus.

There remains a need for improved protection of medically fragile patients or patients susceptible to contracting illness, including children and immunocompromised patients. Incorporating HINS light and/or far UVC light into a personal, portable protective device could reduce infection and illness and give illness-susceptible patients and children greater access into their communities (e.g., by providing more protection to the patient and reducing risk of contracting illness from the environment). Currently during difficult cold and flu seasons medically fragile patients, especially children, often need to be kept in isolation or rely on the use medical masks and other less effective measures.

There may also be a need for readily available and effective decontamination or protective devices for use by the general population. In the event of a regional epidemic or worldwide pandemic, for example, there is a need for a non-specific, widely effective, antimicrobial device for decontamination or general protection. Availability of such a device may mitigate or reduce the need for global economic lockdowns, such as those widely implemented in the wake of COVID-19/SARS-COV-2 in 2020.

BRIEF SUMMARY

The system of the present disclosure may provide a portable lighting apparatus using one or more light sources to project bactericidal and/or virucidal light around all or a portion of the user. The one or more light sources may be LEDs, including high-output LEDs. The projected light in an aspect may be projected over a substantial portion of the user (e.g., conceptualized as a curtain or blanket of light) or over a limited, targeted portion of the user (e.g., conceptualized as a helmet or shield of light covering airways). In one example, the present disclosure may provide such a lighting apparatus that can be rigidly and adjustably mounted to the back of the seat of a wheelchair (such as a power wheelchair) such that the light-emitting portion of the lighting apparatus is placed above the users head and configured to project the light beam(s) downward. Similarly, in another example, a lighting apparatus may be mounted to a support on or adjacent a patient (e.g., a bed rail) and configured to project light on or around a patient. In an optional aspect, such a lighting apparatus can make use of the existing structure (of the wheelchair, bed, or other convenient structure) and make use of an existing power source (e.g., battery on a wheelchair, outlet in a patient room, or the like).

In another aspect, device(s) and/or method(s) according to the present disclosure may be adapted to be used by people who are not in wheelchairs or substantially confined to a bed, such as through the use of a remote battery pack and forced air-cooling systems, which when combined and assembled can be worn as a backpack. In such an aspect, portable lighting apparatus may be worn like a conventional backpack, and light source(s), such as high-output LEDs, may be configured to project light in one or more wavelengths to surround the user (or a portion of the user) or to surround the airways of the user in a curtain of bactericidal and/or virucidal light. With the use of lightweight materials, the apparatus could be comfortably worn by people who are at high risk of infection (e.g., immunocompromised individuals) or medical personnel in high-risk infectious areas.

In an aspect of the disclosure, one or more light sources may be incorporated into a lighting apparatus, the one or more light sources being configured to emit HINS light or far UVC light. In a further aspect, the light source(s) may include one or more LEDs. In another aspect, LEDs incorporated into a lighting apparatus may be configured to emit both HINS light and far UVC light (for example, in a pattern where some LEDs emit HINS light and other LEDs emit far UVC light, such as in an alternating pattern). In another aspect, a lighting apparatus may be configurable such that the lighting apparatus can emit only HINS light, only far UVC light, or a combination of both HINS light and far UVC light. In another aspect, one or more LEDs may be high-output LEDs. In another aspect, one or more LEDs may be constructed and/or configured to emit light at a band of wavelengths peaking at about 405 nm. In another aspect of the present disclosure, one or more LEDs may be constructed and/or configured to emit light at one or more wavelengths between about 200 nm to about 222 nm. In another aspect, one or more LEDs may be constructed and/or configured to emit light at one or more wavelengths peaking at about 205 nm. In another aspect of the present disclosure, high-output LEDs may be constructed and/or configured to emit light at wavelengths (1) of about 405 nm and (2) between about 200 nm to about 222 nm (e.g., through alternating or otherwise mixing the types or configurations of high-output LEDs through the apparatus).

In an aspect of the present disclosure, a protection device may include a lighting apparatus. The lighting apparatus may include a power source electrically coupled to at least one light source. The at least one light source may emit either high-intensity narrow-spectrum electromagnetic energy or far UVC electromagnetic energy when powered. The at least one light source may be configured to project a barrier of electromagnetic energy about at least a portion of an object to be protected when powered.

BRIEF DESCRIPTION OF THE DRAWINGS

The foregoing and other features of the present disclosure will become more fully apparent from the following description, taken in conjunction with the accompanying drawings. Understanding that these drawings depict only several aspects in accordance with the disclosure and are, therefore, not to be considered limiting of its scope, the disclosure will be described with additional specificity and detail through use of the accompanying drawings. One of skill in the art may appreciate that certain features may be optional and that features or aspects of one example may be utilized or combined with other features highlighted in another example. Further, each and every aspect shown and described may not be necessary; rather, various aspects are shown and/or described as potential example features that may be included.

In the drawings.

DETAILED DESCRIPTION

Figure 1:
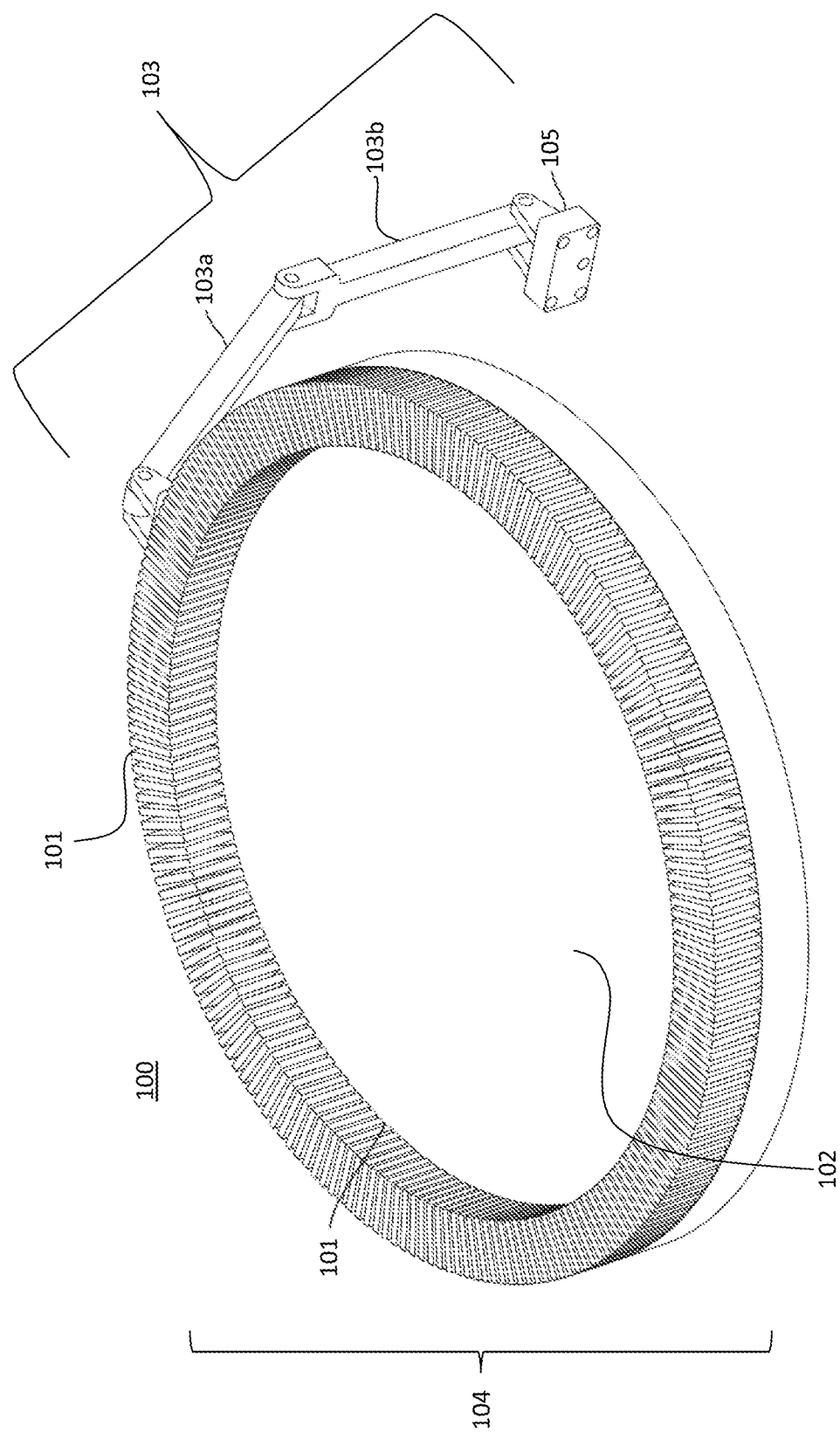
FIG. 1 is a perspective view of an example LED system.

In this detailed description, reference is made to the accompanying drawings, which form a part hereof. In the drawings, similar symbols typically identify similar components, unless context dictates otherwise. The illustrative examples described in the detailed description, drawings, and potential points of novelty are not meant to be limiting. Other aspects may be utilized, and other changes may be made, without departing from the spirit or scope of the subject matter presented here. It will be readily understood that the aspects of the present disclosure, as described herein, and illustrated in the Figures, may be arranged, substituted, combined, and designed in a wide variety of different configurations, all of which are explicitly contemplated and make part of this disclosure.

This disclosure is drawn to methods, systems, devices and/or apparatus related to light emissions for protecting individuals from infection. Aspects of this disclosure are directed to light-emitting devices, including but not limited to light-emitting devices having one or more LEDs as a light source, that emit light having antimicrobial (including antibacterial and/or antiviral) properties. Further aspects of the present disclosure are directed to light-emitting devices that may be configured to be mounted on or near an individual and positioned to emit light covering or surrounding a patient or a portion thereof (such as airways). One or more light sources may emit HINS light, far UVC light, or combinations thereof.

More specifically, some of the disclosed methods, systems, devices and/or apparatus relate to a protection device emitting HINS light and/or far UVC light configured to be used to protect medically fragile children in wheelchairs, other medically fragile people, medical personnel in high risk infectious areas, or (especially in the case of a disease outbreak) individuals desiring enhanced protection from airborne environmental infection. In some aspects, a lighting system may be used to provide protection from harmful pathogens in the air from reaching (or by killing, attenuating, sterilizing, or weakening the pathogens before reaching) the users eyes, nose, or mouth by providing a curtain of antimicrobial light around the user or a portion thereof (such as the head). In specific aspects, a lighting system may have light sources emitting light in particular wavelengths having antimicrobial properties. In even more specific aspects, light sources may include one or more LEDs. Light source(s) may emit HINS light, far UVC light, or some combination thereof. Emitted light may form a protective light barrier in front of or around an individual user. Additional benefit may be found by decontaminating the air around the light emitting device and objects that the curtain of light comes in contact with. In some aspects, a light emitting device may provide additional benefit by decontaminating objects that are passed to a user of a light emitting device (e.g., an individual surrounded at least in part by light) that the light comes in contact with.

With reference to FIG. 1, aspects of a potentially portable, mountable, light-emitting antimicrobial protection device 100 are shown. Protection device 100 may be mountable near an individual user, such as on or near a bed (e.g., a hospital bed) or on a wheelchair. Protection device 100 may include one or more heat sinks 101. In an aspect (not pictured), protection device 100 may include an area 102 at or near the top of the protection device 100 (e.g., above heat sinks 101 or below heat sinks 101 but above the other components) that is enclosed from the environmental air, which may help to prevent pathogens from traveling though the protection device 100. Heat sink(s) 101 may provide increased surface area to direct thermal energy away from light source(s). Protection device 100 may include a support arm 103. Support arm 103 may be constructed of a substantially rigid material such as a metal or plastic. Support arm 103 may connect, at an upper end, to a lighting apparatus portion 104 (note that FIG. 1 omits other aspects of the lighting apparatus portion) and, at a lower end, to a mounting bracket 105. In an aspect, support arm 103 may comprise a plurality of support arm portions 103*a*, 103*b* adjustably connected to each other. As used herein, lighting apparatus portion 104 may also be referred to as lighting apparatus 104. In such an aspect, support arm 103 may be made adjustable by a user to, for example, raise or lower lighting apparatus portion 104 or to reposition lighting apparatus portion 104 so as to project light in an adjustable manner as desired by a user.

Figure 2:
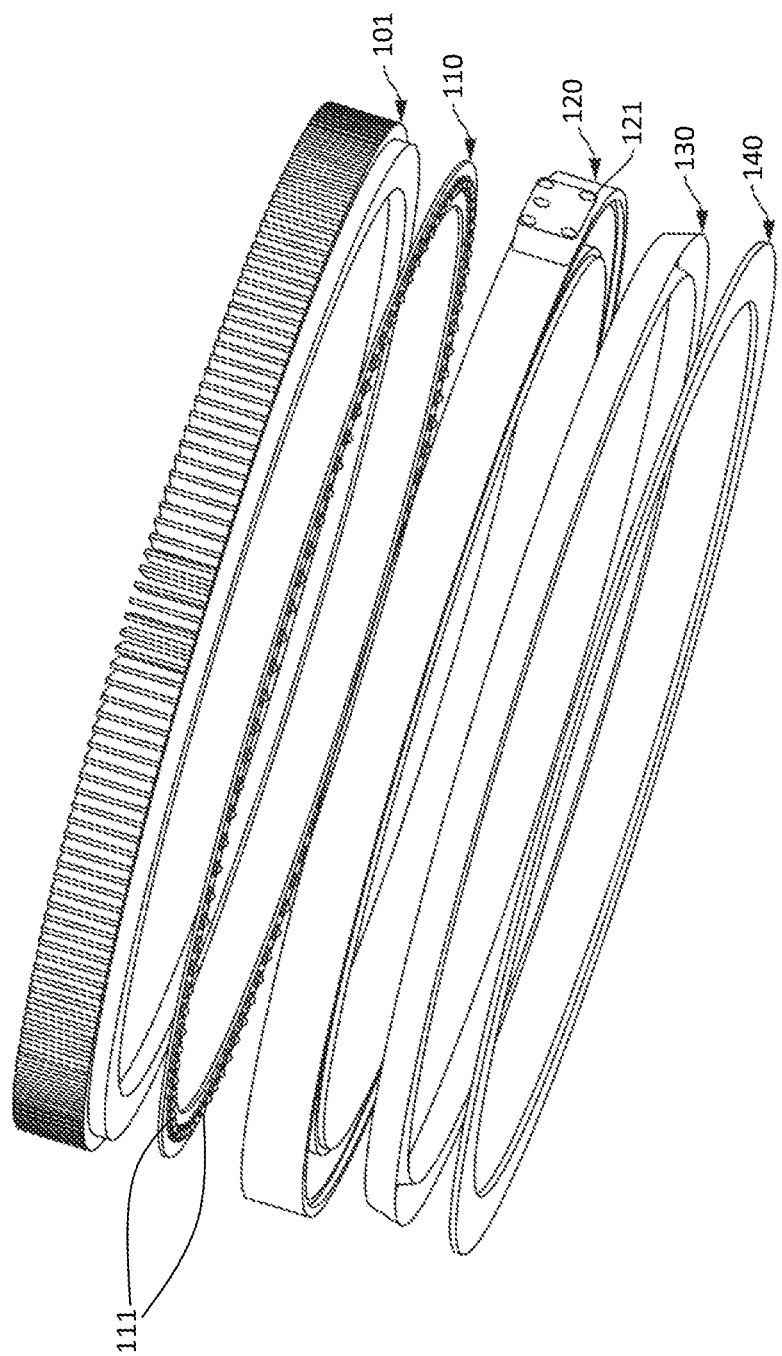
FIG. 2 is an exploded view of an example LED system.

With reference to FIG. 2, aspects of lighting apparatus portion 104 that may be configured for use on a light-emitting, antimicrobial protection device 100 are shown. Lighting apparatus portion 104 may include one or more heat sink(s) 101 thermally coupled to a printed circuit board ("PCB") 110. PCB 110 may be configured annularly as a ring, as depicted in FIG. 2, but may alternatively be configured in a number of different shapes and sizes, depending on the desired application and positioning of light sources 111. One or more light source(s) 111 may be electrically coupled to PCB 110. In an aspect, the one or more light source(s) 111 may be an array of high output LEDs 111. Where there are a plurality of light sources 111, light sources 111 may be aligned on PCB 110. Where PCB 110 is configured as a ring, light sources 111 may be disposed circularly aligned on PCB 110. Where PCB 110 is configured as a quadrilateral, for example, light sources 111 may be linearly aligned. Other arrangements may be utilized and are within the scope of this disclosure.

In an aspect, one or more light source(s) 111 may comprise one or more LEDs 111. However, other types of light source(s) may be utilized. LEDs 111 may be constructed or configured to emit electromagnetic energy (which may be generally referred to as light) having wavelengths of approximately 405 nm. Such a light source may emit a broader range of electromagnetic energy, but the wavelengths of emitted electromagnetic energy may peak at approximately 405 nm, such as approximately 410 nm or between about 400 nm and 420 nm. LEDs, in an aspect, may be high-output LEDs. Additionally or alternatively, one or more light source(s) 111, which may be one or more LEDs 111, are constructed or configured to emit electromagnetic energy having wavelengths of between about 200 nm to about 225 nm. In an aspect, such a light source may emit electromagnetic energy having wavelengths peaking at about 207 nm to about 222 nm. Alternatively or additionally, one or more light source(s) 111 may comprise at least one light source 111 constructed or configured to emit electromagnetic energy at approximately 405 nm (or between about 400 nm to about 420 nm) and at least another light source 111 constructed or configured to emit electromagnetic energy including wavelengths between about 200 nm to about 225 nm. In such an aspect, light sources 111 emitting different wavelengths may be alternated or otherwise patterned such that, when in operation, the combined light sources 111 emit electromagnetic energy in a protective shield or curtain, the energy forming the protective shield or curtain having wavelengths at both about 405 nm and about 200 nm to about 225 nm. Alternatively or additionally, a controller may be included, wherein a user may selectively control whether only one type of light source 111 is enabled, whether both types of light sources 111 are enabled, or whether all light sources 111 are turned off.

Additionally and optionally, light sources 111 emitting visible light may be included. Visible light may allow a user to visually determine when light sources are on or off and may also allow a user to visually determine approximately where the protective shield or protective curtain of electromagnetic energy is activated and where it ends.

As the example in FIG. 2 shows, PCB 110 including light source(s) 111 may be mounted in or on a base structure 120. In an aspect, PCB 110 may be thermally coupled to base structure 120 which may help in dissipating heat away from light source(s) 111. Base structure 120 may provide structure, shape, and/or support to the lighting apparatus portion 104. In an aspect, base structure 120 may include a mounting boss 121. Mounting boss 121 may allow the lighting apparatus portion 104 to be attached to a support arm portion 103. When the PCB 110 is annularly shaped, base structure 120 may similarly have a ring shape. Lighting apparatus portion 104 may further include a reflector 130, which may be mounted in or on base structure 120 or disposed adjacent base structure 120 opposite PCB 110. Reflector 130 may aid in directing and/or shaping electromagnetic energy emitted from light source(s) 111. Lighting apparatus 104 may, in an aspect, include one or more lens(es) 140. Lens(es) 140 may mounted on or in base structure 120. Lens[es] 140 may be configured to focus and/or shape the electromagnetic energy emitted from light source. In an aspect, one or more heat sinks 101 may be coupled to one side of PCB 110, while light source(s) 111 may be coupled to the opposite side of PCB 110. In an aspect, heat sink(s) 101 may be thermally coupled to the light source(s) 111 (which may include a thermal coupling through a via in PCB 110 or, alternately, the PCB 110 may include one or more holes in which a light source 111 may be thermally coupled to at least a part of a heat sink 101). Light source(s) 111 may all emit electromagnetic energy having wavelengths at about 405 nm or between about 400 nm to about 420 nm. In an alternate aspect, light source(s) 111 may all emit electromagnetic energy having wavelengths at about 200 nm to about 222 nm. In an alternate aspect, some of light source(s) 111 may emit electromagnetic energy having wavelengths at about 405 nm and other light source(s) 111 may emit electromagnetic energy having wavelengths at about 207 nm to about 222 nm. In an aspect, light sources 111 having different emitted wavelengths of electromagnetic energy can be configured to operate simultaneously or can be configured to alternate such that only the light source(s) emitting approximately the same wavelengths of electromagnetic energy operate at once.

Figure 3:
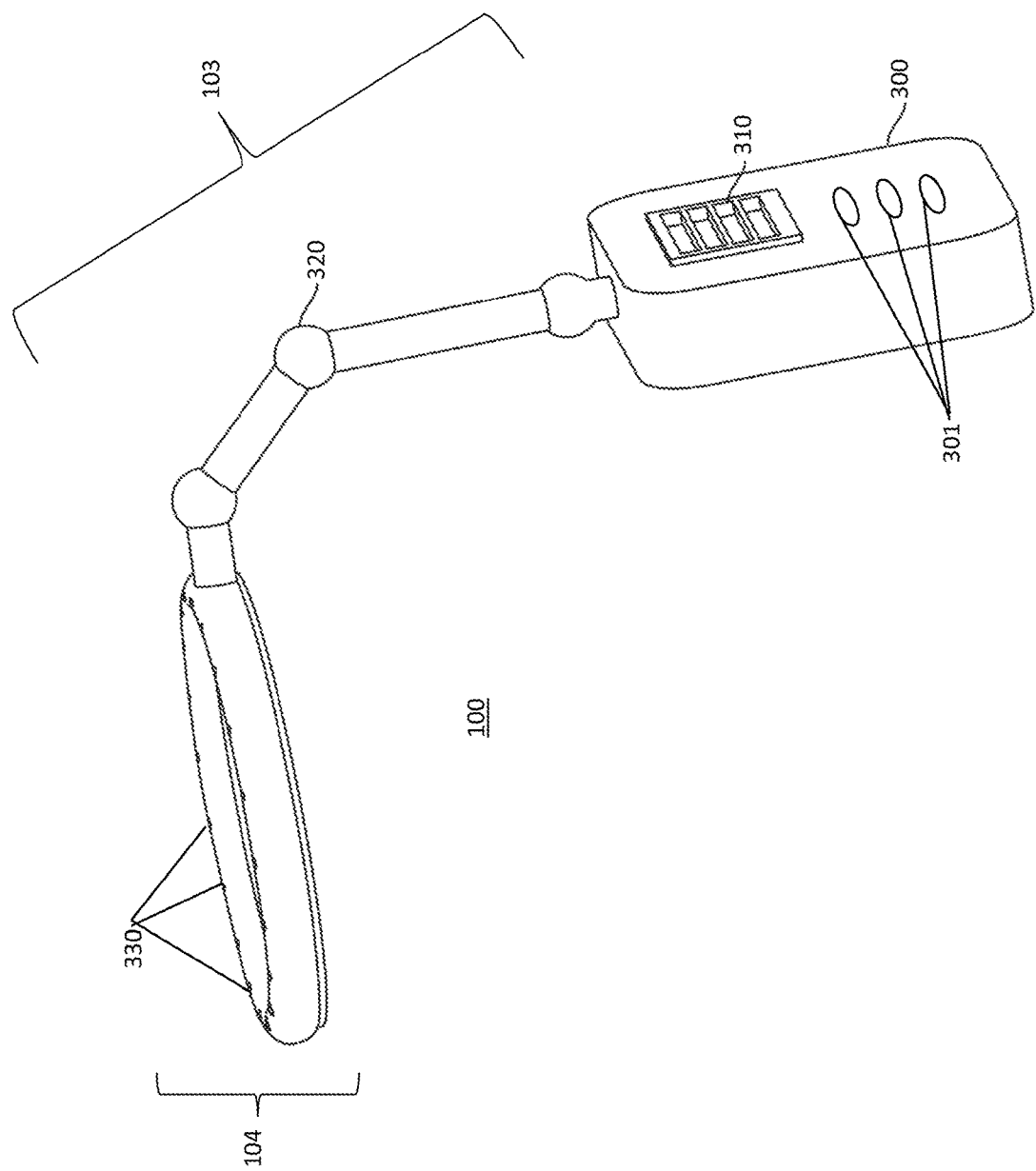
FIG. 3 is a perspective view of an example LED system.
Figure 4:
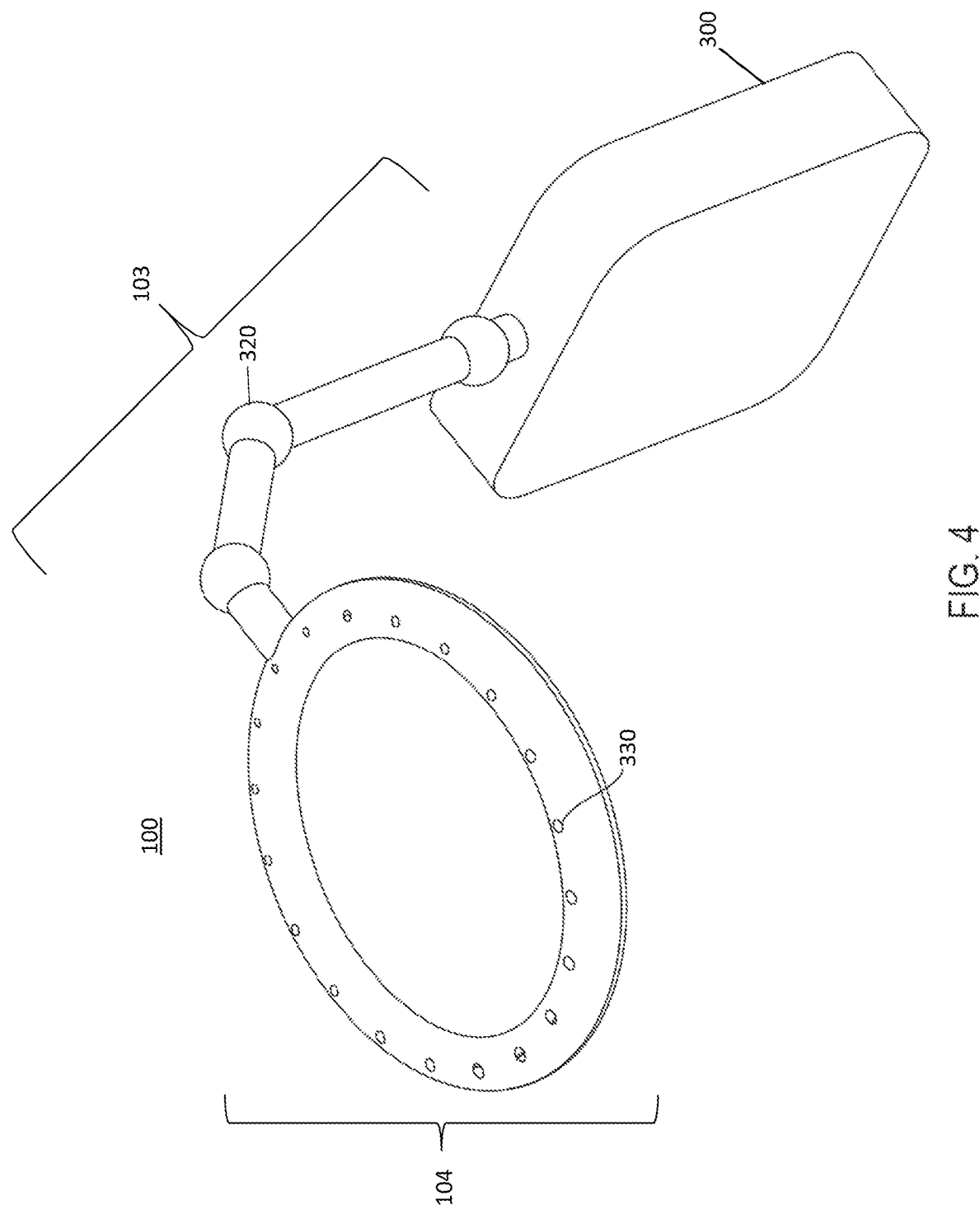
FIG. 4 is an alternate perspective view of an example LED system.
Figure 5:
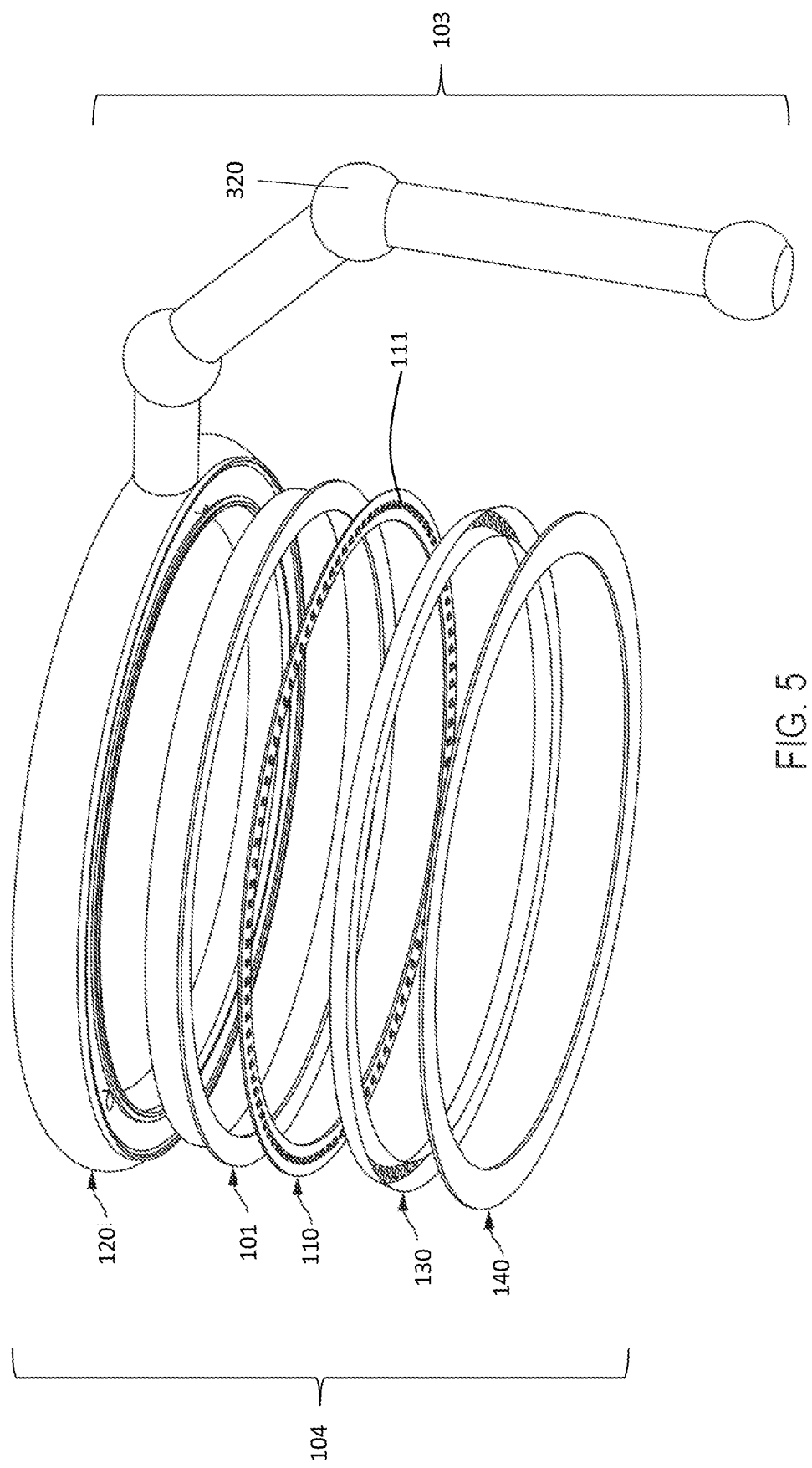
FIG. 5 is an alternate exploded view of an example LED system.

As shown in the examples of FIGS. 3-5, protection device 100 may include a support arm portion 103 coupled to a controller 300 at one end and a lighting apparatus 104 at the other end. Support arm portion 103 may articulate and/or be positionable by a user to adjust the lighting apparatus 104 relative to the controller 300, which may allow a user to adjustably direct emitted electromagnetic energy from lighting apparatus 104.

In an aspect, protection devices 100 according to the present disclosure may include a controller 300 having one or more buttons, switches, touchscreens, or other means 301 of allowing a user to toggle the protection device 100 on and off, selectively activate one or more light source(s) 111 emitting electromagnetic energy of a first wavelength (or band of wavelengths), selectively activate one or more light source(s) 111 emitting electromagnetic energy of a second wavelength (or band of wavelengths), and/or to selectively operate all light sources 111 on protection device 100.

In an aspect, protection devices 100 according to the present disclosure may be mountable. In a more specific aspect, protection device 100 may be configured to be mounted to a wheelchair or a power wheelchair. A controller for protection device 100 may be installed on the wheelchair such that the controller is within easy reach of a wheelchair user or may alternatively be integrated into an existing wheelchair controller. Supporting arm portion 103 may be adjusted such that lighting apparatus portion 104 is disposed over the head of a user. When activated, protection device may emit powerful beams of electromagnetic energy from the lighting apparatus around the users head, in front of and/or to the sides of the user's airways, or another pattern that may be determined by the configuration of light source(s) 111 and/or positioning of the lighting apparatus 104, effectively projecting a protective, antimicrobial (antibacterial or antiviral) curtain or bubble of electromagnetic energy about the user or a portion thereof. Emitted electromagnetic energy may generally be harmful to bacteria and/or viruses while remaining safe to larger organisms such as humans and household pets.

In an aspect, protection device 100 may have an integrated power source such as a battery, while in another aspect, protection device 100 may be wired to an external power source, such as a wheelchair battery, wall outlet, or other external power source.

In an aspect, protection device 100 may be mountable on (or configured to be disposed, in part, within) a backpack. Protection device 100 may include a remote rechargeable battery pack. In an aspect, protection device 100 may include an integrated fan (e.g., as may be visualized by fan vent 310), which fan may be configured to direct cool air taken in via fan vent 310 through an adjustable air channel, to and through support arm portion 103 (which support arm portion can be adjustable at pivot point(s) 320), and to and through the lighting apparatus 104. Air circulated by fan can thus provide additional cooling to PCB 110 and/or light source(s) 111. In aspects where protection device 100 includes heat sink(s) 101, air circulated by the fan can be directed to pass over and/or through heat sink(s) 101 to direct heat out of heat sink(s) 101 and away from light source(s) 111 by convection. Air may then escape out of air vent(s) 330, which may be disposed along the top of lighting apparatus 104.

In some examples a protection device 100 for backpack mounting, which may be similar to depictions in FIGS. 3-5, may include a lighting apparatus 104 constructed of lightweight materials. Lighting apparatus 104 may include a closed center to prevent potential environmental pathogens from traveling though the top of the device. Protection device 100 may include a lightweight heat sink ring 101, which may be thermally coupled to a PCB ring 110 electrically coupled to an array of circumferentially aligned light sources 111 (such as LEDs and/or high-output LEDs). Light sources may emit electromagnetic energy at (a) a wavelength of about 405 nm, (b) a wavelength between about 400 nm and about 420 nm, (c) a wavelength between about 200 nm to about 230 nm, and/or (d) a wavelength between about 207 nm to about 222 nm. PCB 110 and light source(s) 111 may be mounted in or adjacent to a reflector 130 and may be thermally coupled to reflector 130. Reflector 130 may aid in directing and shaping the beams of electromagnetic energy for greatest efficacy. Additionally or alternatively, lens 140 can be mounted as part of lighting apparatus 104 can also be used to direct, focus, and/or shape the beams of electromagnetic energy.

In an aspect, one or more heat sinks 101 may be coupled to one side of the PCB 110 while light sources 111 (such as LEDs) may be coupled to the opposite side of the PCB 110. In an aspect, the heat sink(s) 101 may be thermally coupled to the light sources 111 through a via through the PCB 110 or, in an alternate aspect, the PCB 110 may include a hole in which a light source 111 may be coupled to one or part of one heat sink 101. Light sources 111 may all emit electromagnetic energy having wavelengths at about 405 nm. In an alternate aspect, light sources 111 may all emit electromagnetic energy having wavelengths at about 207 nm to about 222 nm. In an alternate aspect, some of light sources 111 may emit electromagnetic energy having wavelengths at about 405 nm and other light sources 111 may emit electromagnetic energy having wavelengths at about 207 nm to about 222 nm. In an aspect, light sources 111 configured such that some light sources emit electromagnetic energy at a first wavelength and other light sources emit electromagnetic energy at a second wavelength, wherein all light sources 111 can be selectively configured to operate simultaneously or can be selectively configured to alternate such that only the light sources emitting approximately the same wavelengths of electromagnetic energy operate at once.

Figure 6:
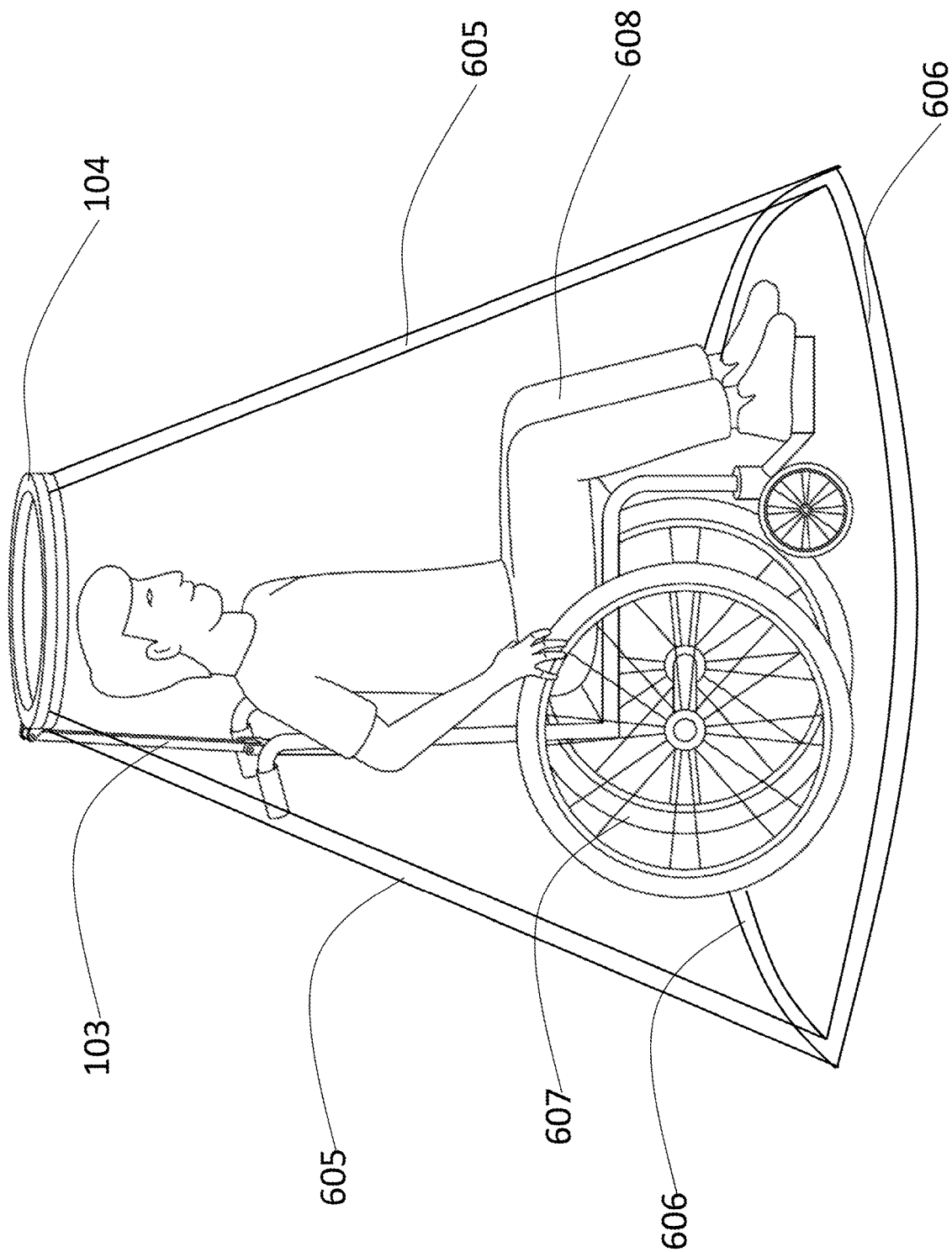
FIG. 6 is an illustration showing an example LED system in use by a user in a wheelchair.

FIG. 6 depicts a user 608 sitting in a wheelchair 607 using an example LED system according to one or more aspects of the present disclosure. Support arm 103 may be attached at one end to wheelchair 607. Lighting apparatus portion 104 may be disposed above the head of user 608. Light sources (e.g., LEDs) in lighting apparatus portion 104 may be configured to project a three-dimensional barrier 605 of electromagnetic energy about user 608. Three-dimensional barrier 605 of electromagnetic energy may travel until incident on a surface 606 of the ambient environment. In such a manner, a focused three-dimensional barrier 605 of electromagnetic energy (which may be conceptualized as a curtain surrounding user 608) may be formed. It should be noted that the three-dimensional barrier 605 of electromagnetic energy as shown in FIG. 6 may not be drawn to scale (e.g., three-dimensional barrier 605 of electromagnetic energy may be narrower) but illustrated to shown concepts described herein.

Figure 7:
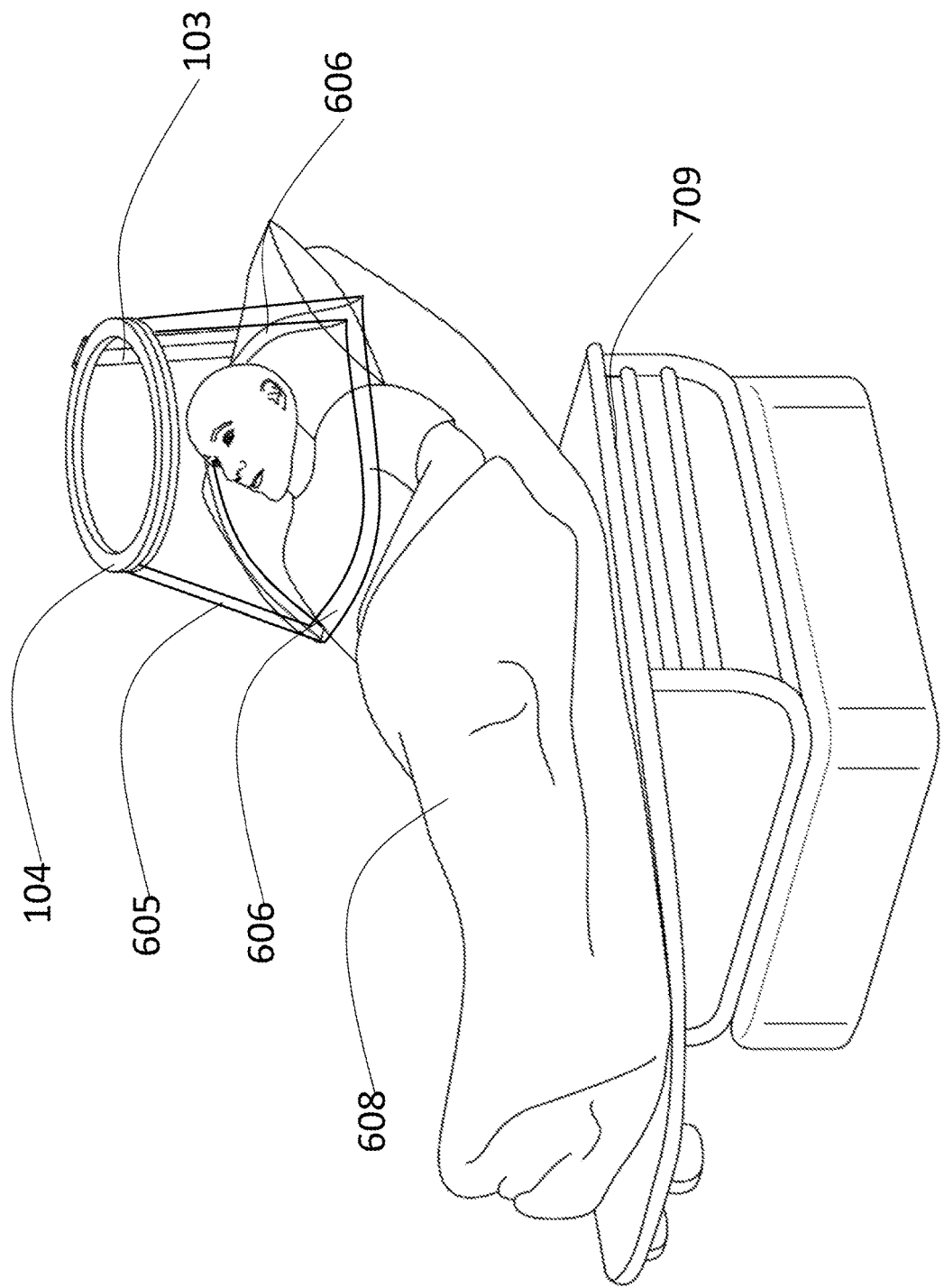
FIG. 7 is an illustration showing an example LED system in user by a user in a bed.

FIG. 7 depicts a user 608 laying in a bed 709 using an example LED system according to one or more aspects of the present disclosure. Support arm 103 may be attached at one end to bed 709. Lighting apparatus portion 104 may be disposed above the head of user 608. Light sources (e.g., LEDs) in lighting apparatus portion 104 may be configured to project a three-dimensional barrier 605 of electromagnetic energy about user 608 or portion thereof (e.g., a head). Three-dimensional barrier 605 of electromagnetic energy may travel until incident on a surface 606 of the ambient environment. In such a manner, a focused three-dimensional barrier 605 of electromagnetic energy (which may be conceptualized as a curtain surrounding user 608 or portion thereof) may be formed. It should be noted that the three-dimensional barrier 605 of electromagnetic energy as shown in FIG. 7 may not be drawn to scale (e.g., three-dimensional barrier 605 of electromagnetic energy may be narrower) but illustrated to shown concepts described herein.

In one aspect of the present disclosure, one or more LEDs may be used in apparatus of the present disclosure and may be configured to emit light or electromagnetic energy at one or more wavelengths that kills or reduces the toxicity/infectiousness/virality/vitality of *C. difficile*, one or more strains of influenza (such as H1N1), one or more coronaviruses (such as 229E, NL63, OC43, HKU1, MERS-COV, SARS-COV, and/or SARS-COV-2), the microorganism causing tuberculosis, respiratory syncytial virus, human parainfluenza viruses, adenoviruses, human metapneumovirus, MRSA, viruses causing the common cold, and other infectious agents.

While various aspects have been disclosed herein, other aspects will be apparent to those skilled in the art. The various aspects disclosed herein are for purposes of illustration and are not intended to be limiting, with the true scope and spirit being indicated by the claims.

What is claimed is:
1. A protection device, comprising:
a lighting apparatus comprising a power source electrically coupled to at least one light source, the at least one light source emitting either high-intensity narrow-spectrum electromagnetic energy or far UVC electromagnetic energy when powered;
wherein the at least one light source is configured to project a three-dimensional barrier of electromagnetic energy about at least a portion of an object to be protected when powered.

2. The protection device of claim 1, wherein the at least one light source is at least one light-emitting diode mounted on a printed circuit board.

3. The protection device of claim 1, wherein the at least one light source is a plurality of light-emitting diodes arranged substantially annularly.

4. The protection device of claim 3, wherein the plurality of light-emitting diodes are configured to project the either high-intensity narrow-spectrum electromagnetic energy or far UVC electromagnetic energy downward to project a three-dimensional barrier of electromagnetic energy surrounding at least a portion of a user disposed under the plurality of light-emitting diodes.

5. The protection device of claim 1, the lighting apparatus further comprising:
   a mounting element having a first mounting surface and an opposing mounting surface, the at least one light source being mounted on the first surface; and
   at least one heat sink thermally coupled to the at least one light source.

6. The protection device of claim 1, wherein the three-dimensional barrier of electromagnetic energy is bactericidal.

7. The protection device of claim 1, wherein the three-dimensional barrier of electromagnetic energy is virucidal.

8. The protection device of claim 4, wherein the three-dimensional barrier of electromagnetic energy is bactericidal.

9. The protection device of claim 4 wherein the three-dimensional barrier of electromagnetic energy is virucidal.

10. The protection device of claim 1, wherein the at least one light source emits electromagnetic energy having a wavelength of about 405 nm when powered.

11. The protection device of claim 1, wherein the at least one light source emits electromagnetic energy having a wavelength of between about 200 nm to about 225 nm when powered.

12. The protection device of claim 1, wherein the at least one light source comprises a plurality of light emitting diodes mounted on a surface of printed circuit board, the plurality of light emitting diodes including a first light emitting diode that emits electromagnetic energy having a wavelength of about 405 nm when powered and a second light emitting diode that emits electromagnetic energy having a wavelength of between about 200 nm to about 225 nm when powered.

13. The protection device of claim 12, the lighting apparatus further comprising a reflector mounted adjacent the light emitting diodes along the optical path of the electromagnetic energy emitted from the light emitting diodes, the reflector being configured to direct the electromagnetic energy emitted from the light emitting diodes.

14. The protection device of claim 13, the lighting apparatus further comprising a lens mounted along the optical path of the electromagnetic energy emitted from the light emitting diodes, the lens being configured to refract the electromagnetic energy emitted from the light emitting diodes.

15. The protection device of claim 14, further comprising an exterior case within which at least a portion of the lighting apparatus is encased.

16. The protection device of claim 15, further comprising a mounting boss disposed on an exterior surface of the exterior case.

17. The protection device of claim 16, further comprising an adjustable support arm that, when adjusted, alters the position of the lighting apparatus, the adjustable support arm having a first end and a second end and attaching at the first end to the mounting boss.

18. The protection device of claim 17, wherein the adjustable support arm is configured to attach at the second end to either a wheelchair or a hospital bed.

19. The protection device of claim 5, wherein the cooling system includes a fan configured to pass air over at least one of the at least one light source, the mounting element, or both the at least one light source and the mounting element, wherein heat is carried away from the at least one light source by convection.

20. The protection device of claim 12, further comprising a controller, the controller making the lighting apparatus selectively operable to power: only the first light emitting diode, only the second light emitting diode, or both the first light emitting diode and the second light emitting diode together.

21. The protection device of claim 20, wherein the at least one light source comprises a plurality of first light emitting diodes and a plurality of second light emitting diodes mounted on the surface of the printed circuit board.

22. The protection device of claim 21, wherein the first light emitting diodes and the second light emitting diodes are alternately mounted on the surface of the printed circuit board.

* * * * *